(12) United States Patent
Pittaro

(10) Patent No.: US 8,150,511 B2
(45) Date of Patent: Apr. 3, 2012

(54) SYSTEMS AND METHODS FOR DETERMINING AN OPTIMAL DEFIBRILLATION SHOCK WAVEFORM

(75) Inventor: Michael R. Pittaro, New Canaan, CT (US)

(73) Assignee: Pacesetter, Inc., Sylmar, CA (US)

( * ) Notice: Subject to any disclaimer, the term of this patent is extended or adjusted under 35 U.S.C. 154(b) by 1205 days.

(21) Appl. No.: 11/824,278

(22) Filed: Jun. 28, 2007

(65) Prior Publication Data

US 2008/0065162 A1    Mar. 13, 2008

Related U.S. Application Data

(60) Provisional application No. 60/818,063, filed on Jun. 29, 2006.

(51) Int. Cl.
    *A61N 1/00* (2006.01)
    *A61B 5/04* (2006.01)
(52) U.S. Cl. .......................... 607/7; 600/518
(58) Field of Classification Search ............... 607/5, 7; 600/518
    See application file for complete search history.

(56) References Cited

U.S. PATENT DOCUMENTS

| | | | |
|---|---|---|---|
| 5,230,336 A | 7/1993 | Fain et al. | |
| 5,275,621 A | 1/1994 | Mehra | |
| 5,431,686 A | 7/1995 | Kroll et al. | |
| 5,500,008 A * | 3/1996 | Fain ................ | 607/5 |
| 5,540,723 A | 7/1996 | Ideker et al. | |
| 5,545,182 A * | 8/1996 | Stotts et al. ........ | 607/5 |
| 5,549,643 A | 8/1996 | Kroll et al. | |
| 5,643,325 A | 7/1997 | Karagueuzian et al. | |
| 5,645,573 A | 7/1997 | Kroll et al. | |
| 5,803,927 A | 9/1998 | Cameron et al. | |
| 5,968,080 A | 10/1999 | Brewer et al. | |
| 6,208,898 B1 | 3/2001 | Gliner et al. | |
| 6,263,239 B1 * | 7/2001 | Brewer et al. ........ | 607/5 |
| 6,628,986 B1 | 9/2003 | Mouchawar et al. | |
| 6,675,042 B2 | 1/2004 | Swerdlow et al. | |
| 6,751,502 B2 | 6/2004 | Daum et al. | |
| 6,859,664 B2 | 2/2005 | Daum et al. | |
| 6,904,314 B1 | 6/2005 | Brewer et al. | |
| 6,931,281 B2 | 8/2005 | Bradley et al. | |
| 7,072,715 B1 | 7/2006 | Bradley | |
| 7,076,295 B1 | 7/2006 | Kroll | |
| 7,643,877 B2 | 1/2010 | Dujmovic, Jr. et al. | |
| 2001/0053925 A1 | 12/2001 | Ideker et al. | |
| 2003/0195580 A1 | 10/2003 | Bradley et al. | |
| 2004/0088017 A1 | 5/2004 | Sharma et al. | |
| 2005/0059897 A1 | 3/2005 | Snell et al. | |
| 2005/0107834 A1 * | 5/2005 | Freeman et al. ..... | 607/5 |

\* cited by examiner

*Primary Examiner* — Nicole F Lavert

(57) ABSTRACT

Embodiments of the invention present methods and systems for determining an optimal defibrillation shock waveform for application to the heart of a patient to stop a rhythm abnormality such as ventricular fibrillation or ventricular tachycardia. Such methods and systems may include measuring and/or collecting information for a cardiac waveform of a patient, produced as a result of either an electrical stimulus applied to a heart of the patient, which may be a pacing shock/stimulus and/or a defibrillation shock waveform, or as the result of intrinsic cardiac activation, determining a characteristic of the cardiac waveform, comparing the determined characteristic of the cardiac waveform to a plurality of values for the characteristic with optional reference to the defibrillator system impedance, wherein each value of the characteristic is associated with a predetermined value for a parameter of an optimal defibrillation shock waveform, and selecting the predetermined value for the parameter of the optimal defibrillation shock waveform based on the comparison.

71 Claims, 12 Drawing Sheets

|   | | Block #1 | | | Block #2 | | Block #3 | |
|---|---|---|---|---|---|---|---|---|
|   | Typical | patient (T=3.5 ms) | | | (T=2.5 ms) | | (T=4.5 ms) | |
| R (Ω) | P1 (ms) | P1 tilt | P2 (ms) | P2 tilt | P1 (ms) | P2 (ms) | P1 (ms) | P2 (ms) |
| 30 | 3.5 | 68% | 3.5 | 68% | 3.0 | 2.5 | 3.5 | 3.5 |
| 32 | 3.5 | 65% | 3.5 | 65% | 3.0 | 2.5 | 4.0 | 4.0 |
| 34 | 3.5 | 63% | 3.5 | 63% | 3.0 | 2.0 | 4.0 | 4.0 |
| 36 | 3.5 | 61% | 3.5 | 61% | 3.0 | 2.0 | 4.0 | 4.0 |
| 38 | 3.5 | 59% | 3.0 | 54% | 3.0 | 2.0 | 4.0 | 4.0 |
| 40 | 4.0 | 62% | 3.5 | 57% | 3.0 | 2.0 | 4.5 | 4.5 |
| 42 | 4.0 | 60% | 3.5 | 55% | 3.0 | 2.0 | 4.5 | 4.5 |
| 44 | 4.0 | 59% | 3.0 | 48% | 3.5 | 2.0 | 4.5 | 4.5 |
| 46 | 4.0 | 57% | 3.0 | 47% | 3.5 | 2.0 | 4.5 | 4.5 |
| 48 | 4.0 | 55% | 3.0 | 45% | 3.5 | 2.0 | 4.5 | 4.0 |
| 50 | 4.0 | 54% | 3.0 | 44% | 3.5 | 2.0 | 5.0 | 4.5 |
| 52 | 4.5 | 57% | 3.0 | 43% | 3.5 | 2.0 | 5.0 | 4.0 |
| 54 | 4.5 | 55% | 3.0 | 42% | 3.5 | 2.0 | 5.0 | 4.0 |
| 56 | 4.5 | 54% | 3.0 | 41% | 3.5 | 2.0 | 5.0 | 4.0 |
| 58 | 4.5 | 53% | 3.0 | 39% | 3.5 | 2.0 | 5.0 | 4.0 |
| 60 | 4.5 | 52% | 3.0 | 38% | 4.0 | 2.0 | 5.5 | 4.0 |
| 62 | 4.5 | 51% | 3.0 | 37% | 4.0 | 2.0 | 5.5 | 4.0 |
| 64 | 4.5 | 49% | 3.0 | 37% | 4.0 | 2.0 | 5.5 | 4.0 |
| 66 | 5.0 | 52% | 3.0 | 36% | 4.0 | 2.0 | 5.5 | 4.0 |
| 68 | 5.0 | 51% | 3.0 | 35% | 4.0 | 2.0 | 5.5 | 4.0 |
| 70 | 5.0 | 50% | 3.0 | 34% | 4.0 | 2.0 | 5.5 | 4.0 |
| 72 | 5.0 | 49% | 3.0 | 33% | 4.0 | 2.0 | 5.5 | 3.5 |
| 74 | 5.0 | 48% | 3.0 | 33% | 4.0 | 2.0 | 6.0 | 4.0 |
| 76 | 5.0 | 47% | 3.0 | 32% | 4.0 | 2.0 | 6.0 | 4.0 |
| 78 | 5.0 | 46% | 2.5 | 27% | 4.0 | 2.0 | 6.0 | 4.0 |

FROM
FIG. 3-1

| 80  | 5.0 | 45% | 2.5 | 26% | 4.5 | 2.0 | 6.0 | 3.5 |
|-----|-----|-----|-----|-----|-----|-----|-----|-----|
| 82  | 5.5 | 48% | 3.0 | 30% | 4.5 | 2.0 | 6.0 | 3.5 |
| 84  | 5.5 | 47% | 3.0 | 29% | 4.5 | 2.0 | 6.0 | 3.5 |
| 86  | 5.5 | 46% | 3.0 | 29% | 4.5 | 2.0 | 6.0 | 3.5 |
| 88  | 5.5 | 45% | 2.5 | 24% | 4.5 | 2.0 | 6.5 | 3.5 |
| 90  | 5.5 | 45% | 2.5 | 24% | 4.5 | 2.0 | 6.5 | 3.5 |
| 92  | 5.5 | 44% | 2.5 | 23% | 4.5 | 2.0 | 6.5 | 3.5 |
| 94  | 5.5 | 43% | 2.5 | 23% | 4.5 | 2.0 | 6.5 | 3.5 |
| 96  | 5.5 | 43% | 2.5 | 22% | 4.5 | 2.0 | 6.5 | 3.5 |
| 98  | 5.5 | 42% | 2.5 | 22% | 4.5 | 2.0 | 6.5 | 3.5 |
| 100 | 5.5 | 41% | 2.5 | 22% | 4.5 | 2.0 | 6.5 | 3.5 |
| 102 | 6.0 | 44% | 2.5 | 21% | 4.5 | 2.0 | 6.5 | 3.5 |
| 104 | 6.0 | 43% | 2.5 | 21% | 4.5 | 2.0 | 6.5 | 3.5 |
| 106 | 6.0 | 42% | 2.5 | 20% | 5.0 | 2.0 | 7.0 | 3.5 |
| 108 | 6.0 | 42% | 2.5 | 20% | 5.0 | 2.0 | 7.0 | 3.5 |

FIG. 3-2

| FIG. 4-1 | FIG. 4-3 | FIG. 4-5 |
| FIG. 4-2 | FIG. 4-4 | FIG. 4-6 |

FIG. 4

| Patient # | F | G | Block 1+ | Block 1- | PW 1 | Imp 1 | Block 2+ | Block 2- | PW 2 |
|---|---|---|---|---|---|---|---|---|---|
| 1 | | .2 | 30 | | | | | | |
| 2 | | 1.5 | 20 | | | | | | |
| 3 | | 2.6 | 20 | | | | | | |
| 4 | | .3 | 40 | | | | | | |
| 5 | | 3.3 | 50 | | 3.5/3.5 | 35 | | | |
| 6 | | 4.8 | 50 | | 4.0/3.5 | 41 | 400 | | 3.0/2.0 |
| 7 | | 4.7 | 50 | | 3.5/3.5 | 30 | 400 | | 3.5/2.0 |
| 8 | | 5.8 | 50 | | 3.5/3.0 | 37 | 450 | | 3.0/2.0 |
| 9 | | 4 | 70 | | 4.0/3.0 | 40 | 600 | | 3.0/2.0 |
| 10 | | 8.1 | 50 | | 3.5/3.5 | 30 | 350 | | 3.5/2.0 |
| 11 | 17.2/7.35 | | 80 | | 3.5/3.5 | 32 | 550 | | 3.0/2.0 |
| 12 | | 3.8 | 70 | | 3.5/3.5 | 37 | 300 | | 3.5/2.5 |
| 13 | | 19.6 | 40 | | | | 550 | 500 | 3.0/2.5 |
| 14 | | 2.9 | 100 | | | | 350 | | 3.0/2.0 |
| 15 | | 4.2 | 70 | 450 | 4.0/3.5 | 41 | 500 | 450 | 3.0/2.0 |
| 16 | | 2.3 | 30 | 450 | 3.5/3.0 | 36 | 830 | 600 | 3.0/2.0 |
| 17 | | 3.3 | 60 | | 3.5/3.0 | 37 | 830 | 700 | 3.0/2.0 |
| 18 | | 3.7 | 45 | 450 | 4.0/3.0 | 44 | 300 | | 3.5/2.5 |
| 19 | | | 45 | | 4.0/3.5 | 44 | 830 ???? | | 3.0/2.0 |
| 20 | 6.0/16.0 | | 30 | | | | 450 | | 3.0/2.0 |
| 21 | 12.0/20.0 | | 60 | 300 | 3.5/3.5 | 32 | 650 | 450 | 3.0/2.0 |
| 22 | | 4.2 | 50 | 400 | 4.0/3.5 | 42 | 450 | 400 | 3.0/2.0 |
| 23 | 3.9/9.1 | | 30 | | 3.5/3.0 | 37 | 400 | | 3.0/2.0 |
| 24 | | 3.3 | 60 | | 4.0/3.5 | 40 | 650 | 600 | 3.0/2.0 |
| 25 | | 1.3 | 20 | | 4.5/3.0 | 49 | 350 | | 3.5/2.0 |
| 26 | | 1.8 | 35 | | 3.5/3.0 | 39 | 350 | | 3.0/2.0 |

| | | | | | | | |
|---|---|---|---|---|---|---|---|
| 27 | 2.3 | 45 | 500 | | | | |
| 28 | 12.3 | 40 | 400 | | | | |
| 29 | 4.2 | 50 | 400 | | | | |
| 30 | 6.6 | 80 | 700 | 4.3/4.3 | 350 | | |
| 31 | 3.1 | 40 | 830 | 3.5/3.5 | 33 | 500 | 3.0/2.0 |
| 32 | 7.4 | 70 | 550 | 4.0/3.5 | 31 | 500 | 3.0/2.0 |
| 33 | 4.1 | 30 | 550 | 4.0/3.5 | 38 | 400 | 3.0/2.0 |
| 34 | 4.4 | 70 | 450 | 4.0/3.0 650 | 41 | 600 | 3.0/2.0 |
| 35 | 3.75 | 60 | 600 | 4.0/3.0 550 | 42 | 650 | 3.0/2.0 |
| 36 | 2.1 | 60 | | 4.0/3.0 500 | 35 | 550 | 3.5/2.0 |
| 37 | 3.1 | 50 | 350 | 4.0/3.0 300 | 48 | 300 | 3.0/2.0 |
| 38 ??? | ??? | | 300 | | 43 | 600 | 3.5/2.0 |
| 39 | 6.3 | 50 | 700 | 4.0/3.5 | 39 | 400 | 3.0/2.0 |
| 40 | 2.7 | 60 | 450 | 4.5/3.0 | | 400 | 3.0/2.0 |
| 41 | 2.1 | 50 | 350 | 3.5/3.0 399 | 37 | 300 | 3.0/2.0 |
| 42 | 4.3 | 60 | 250 | 4.5/3.0 | 37 | 350 | 3.5/2.0 |
| 43 | 5 | 50 | 300 | 4.0/3.0 | 60 | 350 | 3.5/2.0 |
| 44 | 3.9 | 70 | 650 | 4.0/3.5 200 | 49 | 250 | 3.5/2.0 |
| 45 | 6.3 | 50 | 600 | 4.0/3.0 | 44 | 300 | 3.0/2.0 |
| 46 | 4.2 | 50 | 300 | 3.5/3.0 550 | 40 | 650 | 3.0/2.0 |
| 47 | 2.1 | 50 | 450 | 4.5/3.0 | 43 | 600 | 3.0/2.0 |
| 48 | 6.5 | 60 | 350 | 4.0/3.0 | 37 | | 3.0/2.0 |
| 49 | 103/69 60/120 | | 830 | 3.5/3.5 550 | 39 | 450 | 3.5/2.0 |

FROM FIG. 4-1

FROM FIG. 4-1 → / TO FIG. 4-5 →

| Imp 2 | Block 3+ | Block 3- | PW 3 | Imp 3 | 65% + | 65% - | PW65% | Imp 65% | P Bst | F |
|---|---|---|---|---|---|---|---|---|---|---|
| 32 | | | | | 830 | 537 | 4.5/4.5 | 33 | | 2 |
| 47 | | | | | 830 | 490 | 5.4/5.4 | 47 | | 2 |
| 35 | | | | | 693 | 537 | 4.8/4.8 | 35 | | 2 |
| 43 | | | | | 635 | 551 | 3.2/3.2 | 41 | Not 2 | |
| 50 | | | | | 338 | | 6.1/6.1 | 44 | Not 2 | 2 |
| 41 | | | | | 537 | ?10J | ?? | | | |
| 30 | | | | | 338 | | | | | |
| 36 | 500 | | 4.0/4.0 | 37 | 537 | | 4.3/4.3 | 32 | Not 2 | 2 |
| 41 | | | | | 338 | | 4.8/4.8 | 37 | Not 2 | 2 |
| 30 | | | | | 436 | | 5.5/5.5 | 40 | Not 2 | 2 |
| 31 | | | | | 619 | | 3.8/3.8 | 30 | Not 2 | 2 |
| 39 | | | | | 693 | | 4.6/4.6 | 33 | Not 2 | 2 |
| 46 | | | | | 338 | 619 | 4.5/4.5 | 35 | Not 2 | 2 |
| | | | | | 277 | | 5.9/5.9 | 44 | Not 2 | |
| 42 | 500 | | 4.5/4.5 | 41 | 830 | | 4.6/4.6 | 33 | | 2 |
| 37 | | | | | 830 | 490 | 5.7/5.7 | 42 | Not 2 | |
| 37 | 400 | | 4.0/4.0 | 39 | 392 | 436 | 4.9/4.9 | 38 | | |
| 43 | 550 | | 4.5/4.5 | 44 | 490 | | 5.2/5.2 | 40 | | 2 |
| 44 | | | | | 537 | 436 | 5.5/5.5 | 43 | Not 2 | 2 |
| | | | | | | | 5.5/5.5 | 43 | Not 2 | |
| 32 | 400 | | 4.5/4.5 | 42 | 436 | 311 | 4.1/4.1 | 33 | Not 2 | 2 |
| 42 | | | | | 392 | | 5.2/5.2 | 42 | Not 2 | 2 |
| 39 | | | | | 392 | | 4.9/4.9 | 37 | Not 2 | |
| 39 | 600 | | 4.5/4.5 | 40 | 693 | 656 | 5.2/5.2 | 39 | Not 2 | |
| 51 | 350 | | 5/4.5 | 51 | 436 | | 6.7/6.7 | 52 | Not 2 | |
| 39 | 350 | | 4.0/4.0 | 40 | 392 | | 5.1/5.1 | 38 | Not 2 | |

| P Bst G | Best | | RES F | RES G | |
|---|---|---|---|---|---|
| Not 2 | 2 | 2>65 | ** | pos | pos | ** |
| Not 2 | 2 | 2>65 | ** | pos | pos | ** |
| Not 2 | 2 | 2>?1>65 | ** | pos | pos | ** |
| Not 2 | | 2 equiv 65 | | pos | pos | |
| Not 2 | | 2 equiv 65 | | pos | pos | |
| Not 2 | | 2,1,65 eq | ** | pos | pos | ** |
| Not 2 | | 2,1,65 eq | ** | pos | pos | ** |
| Not 2 | | 1>3/65/2 | ** | pos | pos | ** |
| Not 2 | | 1>2,65 | ** | pos | pos | ** |
| Not 2 | | 65>1,2 | ** | pos | pos | ** |
| Not 2 | | 1,65>2 | ** | pos | pos | ** |
| Not 2 | | 1,65>2 | ** | pos | pos | ** |
| Not 2 | | 2 equiv 65 | ** | pos | pos | ** |
| Not 2 | | 65 > 2 | ** | pos | pos | ** |
| Not 2 | | 2>1,3>65 | ** | pos | NEG | #### |
| Not 2 | | ? 1>2 | #### | ?pos? | ?NEG? | |
| Not 2 | | 1,3,65>2 | | NEG | pos | ** |
| Not 2 | 2 | 65>1,2,3 | ** | pos | pos | ** |
| Not 2 | | 1,2,65 eq | | pos | pos | |
| Not 2 | 2 | 2?>1,65 | #### | ?NEG? | ?NEG? | #### |
| Not 2 | | 2,3,65>1 | | pos | pos | |
| Not 2 | | 2,65>1 | | pos | pos | |
| | 2 | 1,3>2,65 | | pos | pos | |
| | 2 | 2,3>1,65 | ** | pos | pos | ** |
| | 2 | 1,2,3,65 | | pos | pos | |

FROM FIG. 4-3

| | | | | |
|---|---|---|---|---|
| Not 2 | 65>1,2 | #### | NEG | pos | |
| Not 2 | 1>2,65 | | pos | pos | |
| Not 2 | 1,2,3,65 | | pos | pos | |
| Not 2 | 65,1,3>2 | ** | pos | pos | ** |
| Not 2 | 65>2,3>1 | ** | pos | pos | *** |
| Not 2 | 1,65>2 | ** | pos | pos | |
| | 1,2,65 | | pos | pos | |
| 2 | 2,65>1 | | pos | pos | |
| Not 2 | 1,2,65 | | pos | pos | |
| Not 2 | 2,65 | | pos | pos | |
| Not 2 | 1>2,65 | | pos | pos | |
| Not 2 | 1,2,65 | | pos | pos | |
| Not 2 | 1>2,3,65 | | pos | pos | |
| Not 2 | 2>1,3,65 | ** | pos | pos | #### |
| Not 2 | 1,2>65 | ** | pos | NEG | #### |
| Not 2 | 1,2,65 | | pos | NEG | |
| Not 2 | 1,2,65 | | pos | pos | |
| Not 2 | 1,2,65 | | pos | pos | |
| Not 2 | 1,2,65 | | pos | pos | |
| Not 2 | 1>65,2 | | pos | pos | |
| Not 2 | 65,1,2 | | pos | pos | |
| Not 2 | 1>2,65 | | pos | pos | |
| Not 2 | 65,2>1,3 | | pos | pos | |

FIG. 4-6

SYSTEMS AND METHODS FOR DETERMINING AN OPTIMAL DEFIBRILLATION SHOCK WAVEFORM

CROSS REFERENCE

This application claims the benefit of U.S. Provisional Application No. 60/818,063, filed Jun. 29, 2006, which application is incorporated herein by reference.

FIELD OF THE INVENTION

Embodiments of the present invention are directed to defibrillators and defibrillation, and more particularly, to methods and systems for optimizing defibrillation shock waveforms for defibrillation devices and more particularly, to implantable defibrillation devices.

BACKGROUND

Defibrillation of a heart experiencing ventricular fibrillation (VF) or ventricular tachycardia (VT) occurs by applying a defibrillation shock waveform (DSW) to the heart which presents a large enough voltage gradient across the heart to stop the VF or VT. Such a voltage gradient not only enables the cessation of ventricular fibrillation, but generally re-establishes normal heart rhythm.

Currently, the medical device industry provides implantable cardiac defibrillators (ICDs) from a variety of manufacturers including Medtronic, Inc. and St. Jude Medical, Inc. For example, St. Jude Medical markets ICDs identified by the Photon®, Epic™, Epic™+ and Contour® families. Such examples may be found at the St. Jude Medical website (e.g., www.sjm.com), the information of which, pertaining to such devices, is herein incorporated by reference in its entirety (see also, http://en.wikipedia.org/wiki/Implantable_cardioverter-defibrillator, page was last modified 00:17, 18 Jun. 2006, the entire disclosure of which is herein incorporated by reference in its entirety).

The defibrillation shock waveform (DSW) for such ICDs typically comprises a biphasic waveform pulse, an example of which is illustrated in FIG. 2. As shown, such a biphasic waveform pulse generally comprises two portions: a first positive phase and a second negative phase (though the polarities may be reversed). The "tilt" of the waveform comprises the slope of the first phase and is a function of the duration of that portion of the DSW. The tilt may be viewed as the slope of the difference in voltage of the leading edge compared with the trailing edge of each pulse. Accordingly, as the duration of the first phase increases, for a given impedance, so does the tilt value. Generally, in such ICDs, the tilt or time period for each phase of the biphasic waveform pulse can be adjusted to optimize the DSW for a particular patient. The pulse width duration(s) may be fixed, yielding varying tilts depending on the impedance of the system. Alternatively, the tilt may be fixed, resulting in varying pulse widths depending on the system impedance.

Realizing a "large enough" voltage gradient or threshold to overcome VF using a DSW is dependent upon a number of factors including capacitor size of the defibrillator, maximum voltage, voltage duration of the defibrillator waveform, corresponding shape of the defibrillator waveform, and the arrangement and/or orientation of defibrillation electrodes. Furthermore, characteristics of the cardiac tissue and defibrillator system (ICD) impedance can also play an important role in determining the defibrillation threshold.

The defibrillation threshold may be minimized upon an accurate (i.e., measured) membrane time constant (or chronaxie) of a particular patient's heart. The membrane time constant is a measure of the time it takes for the membrane voltage to reach a new value, and is independent of the strength (voltage, energy or amps) of the shock of the DSW. However, the membrane time constant of the cardiac tissue is not known with precision and cannot be currently measured in vivo.

The impedance of the ICD shock is readily measured and may also influence the time course of the voltage across the cardiac tissue after the start of the shock (i.e., large voltage across the heart). Accordingly, as impedance increases, so does the time for the cardiac tissue to reach maximum value. In addition, the ideal shock duration of the DSW, or other DSW properties, may change as impedance changes.

In defibrillation, one aim is, with a shock of one polarity, to depolarize substantially all the cardiac tissue cells simultaneously or prolong refractoriness, and then remove the charge with a shock of the opposite polarity. However, when longer pulse widths are unnecessarily applied, re-initiation of fibrillation may occur after defibrillation. If a long enough pulse width is not applied, the tissue may not be simultaneously depolarized or have refractoriness prolonged, and fibrillation may persist.

BRIEF DESCRIPTION OF THE FIGURES

FIGS. 3-1 and 3-2 together form a chart illustrating pulse time values for positive and negative phases of a biphasic defibrillation waveform, which may be set in an implantable cardiac device.

FIG. 4 and FIGS. 4-1 through 4-6 together form a chart illustrating patient data according to some of the embodiments of the present invention.

FIG. 5 is a depiction of a system of the invention.

SUMMARY OF THE EMBODIMENTS OF THE PRESENT INVENTION

Embodiments of the present invention are directed to ICDs, examples of which are disclosed in published U.S. patent application Ser. No. 10/437,110 (U.S. publication no. 20040002738), the entire disclosure of which is herein incorporated by reference.

Accordingly, some embodiments of the present invention are able to determine an optimal DSW for a particular patient by analyzing one or more characteristics of the cardiac waveform of the patient. Moreover, in some embodiments, optimal durations for one or both of each phase of the biphasic waveform of a DSW or the optimal tilt of the DSW may be determined by analyzing the one or more characteristics of the cardiac waveform.

By identifying optimal defibrillation waveform variables prior to testing an ICD, a lower defibrillation threshold may be determined. A lower defibrillation threshold may result in safer and shortened defibrillation testing, smaller defibrillator units, a greater margin of safety for successful defibrillation, and more rapid delivery of therapy. In addition, there may be increased device longevity, decreased myocardial tissue damage, improved myocardial function, decreased patient pain, and improved device performance should the optimal waveform change, over the life of the device.

The cardiac waveform which is analyzed may be an intrinsic waveform, that is, a waveform from a heart beat without stimulation, or a waveform generated as a result of an applied electrical stimulus. Such a stimulus may be a pacing stimulus/shock, as well as from a DSW, either of which (of course) may be applied via a ICD. A cardiac waveform generated as the result of such pacing stimulus may be a repeatable, evoked, and/or entrainable response.

Figure 1:
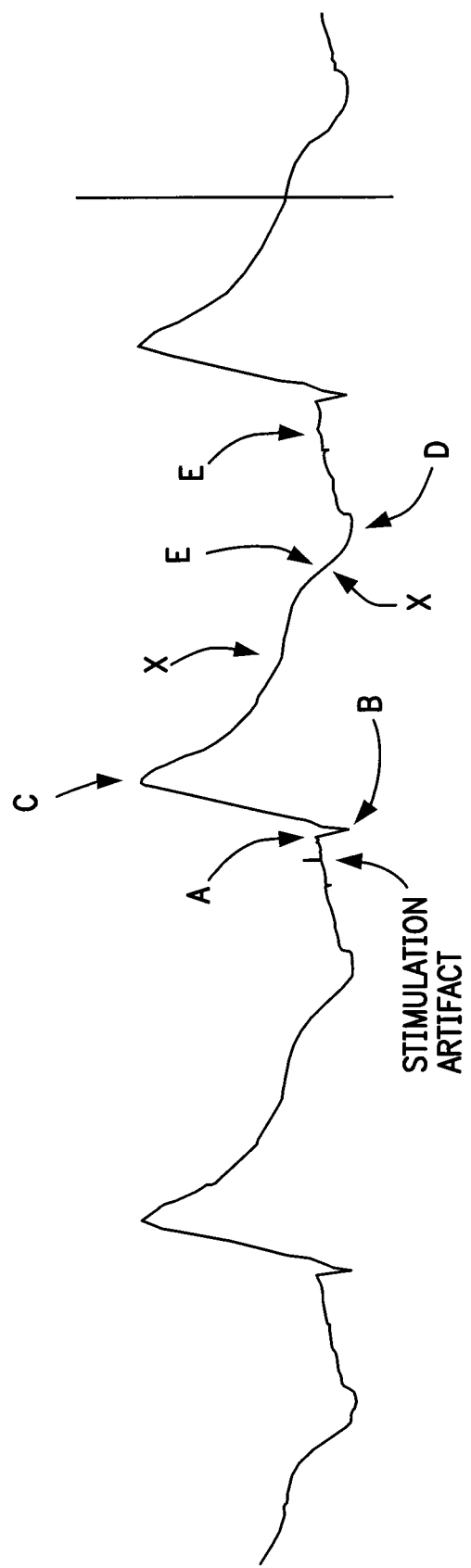
FIG. 1 is an illustration of a cardiac waveform, with noted points of interest, which may be analyzed by some embodiments of the invention.
Figure 2:
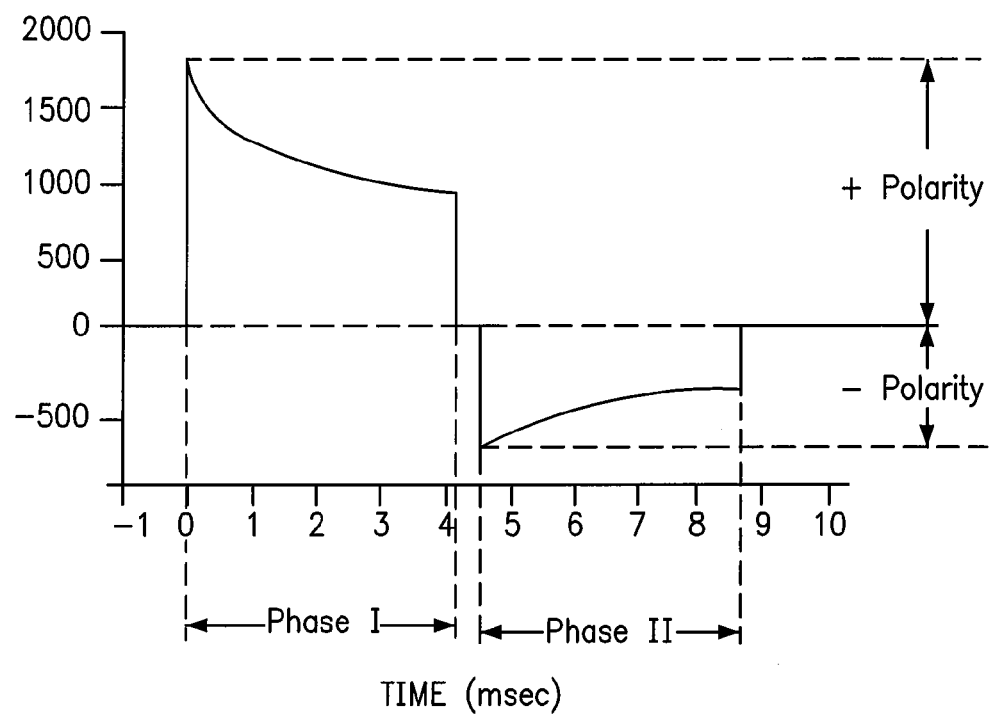
FIG. 2 is a typical illustration of a biphasic waveform for a defibrillation shock waveform typically used in implantable cardiac devices.

For example, in one embodiment of the invention, an ICD applies one or more stimuli/pacing shocks to the heart of a patient. The resulting waveform(s) is then measured and/or the corresponding information/data recorded and/or analyzed to determine one or more characteristics of the cardiac waveform. A cardiac waveform is illustrated in FIG. 1, although one of ordinary skill in the art will recognize that there are many variations of a cardiac waveform and the current waveform is for illustrative purposes, and is not meant to limit the scope of the invention.

As shown, the illustrated cardiac waveform is graphically plotted, where the x-axis comprises time, typically measured in milliseconds, and the y-axis comprises voltage, typically measured in millivolts (for example). Accordingly, in some embodiments of the invention, the waveform data collected may yield the following information in Table I:

TABLE I

| Point/Item | Description |
|---|---|
| A | initial start of deflection |
| B | first trough |
| C | peak |
| D | second trough |
| E | return to baseline or zero crossing |
| F | slope of any portion of the line between points B and C (in, for example, msec/millivolt) |
| G | time period (msec) between points B and C |
| H | time period G divided by the voltage differential (millivolts) between points B and C |
| I | time period (msec) between stimulation to point A |
| J | time period (msec) between stimulation to point B |
| K | time period (msec) between stimulation to point C |
| L | time period (msec) between stimulation to point D |
| M | time period (msec) between stimulation to point E |
| N | time period (msec) between points C and D |
| O | time period (msec) between points C and E |
| P | Slope of any portion of the line between points A and B |
| Q | time period (msec) between points A and B |
| R | time period (msec) between points A and C |
| S | time period (msec) between points A and D |
| T | time period (msec) between points A and E |
| U | Area under the curve (AUC) (e.g., points B, C and D) |
| W | Time period (msec) between any E point and any other point noted. |
| X | An inflection point |
| Y | Time period (msec) between points X and any other point noted |

One of ordinary skill in the art will appreciate that other characteristics of a cardiac waveform other than those listed above may be measured and/or determined, including any mathematical analysis of the waveform or mathematical analysis of characteristics of the waveform. Such mathematical analysis may include one or more of: a Fourier transformation, a Bartlett transformation of the cardiac waveform, a wavelet analysis, and a relationship between characteristics and/or a relationship of the results of a mathematical analysis (e.g., at least any of the foregoing) of the waveform. Based on the measured, collected and/or determined data, a value of one or more parameters of a DSW for the particular patient can be determined.

The following example of one embodiment of the present invention will be discussed with reference to St. Jude Medical ICDs having adjustable parameter settings for a DSW. In particular, the following example is in reference to St. Jude Medical ICDs using biphasic DSW, where the pulse durations of both phases (positive and negative) or the tilt may be adjustable. In that regard, FIG. 3 is an exemplary chart illustrating the pulse durations P1 and P2 for different impedances of an ICD, as well as associated tilt associated with the particular phase of the biphasic waveform. One of ordinary skill in the art will appreciate that the following described example is not meant to limit the scope of the present invention, but merely to demonstrate at least one embodiment of the invention which may be applicable to one or more other embodiments of the present invention.

The chart illustrated in FIG. 3 is a chart listing pulse durations for a biphasic DSW for one or more defibrillator devices manufactured by St. Jude Medical, Inc. (for example), obtained from a St. Jude document entitled, "ICD Alternative Defibrillation Bi-Phasic Waveform Pulse Width Recommendations" (copyright St. Jude Medical, Inc., 2004), the entire contents of which are herein incorporated by reference ("Pulse Width Publication"). The pulse widths listed in each block preferably correspond to particular defibrillator system impedance values and other defibrillator specific variables (e.g., capacitance), and list P1 (pulse durations of the positive phase of the DSW) and P2 (pulse durations of the negative phase of the DSW) values for three model membrane time constants ($\tau$): 2.5, 3.5 and 4.5 msec (for example). These model membrane time constants were chosen based on in vitro mammalian tissue and cell studies and modeling. However, currently, no information from any institution or manufacturer offers a way to determine which model membrane time constant is optimum for the heart of a particular patient.

The selection of optimal DSW parameters, for example pulse widths or tilts, according to some embodiments of the present invention, may be based on matching a defibrillator waveform to one or more defibrillation characteristics of cardiac tissue (e.g., such as the membrane time constant or a measurement which correlates with the membrane time constant) and additionally, in some embodiments, on characteristics of a defibrillation system, such as impedance and capacitance. Accordingly, if cardiac tissue can be depolarized rapidly, a shorter pulse width is preferably the most efficient way to defibrillate the cardiac tissue, according to some embodiments of the invention. In some embodiments, repolarization may also play an important role in optimum P1 and P2.

Accordingly, in one embodiment of the present invention, for example, G values (see Table I above) of the cardiac waveform measured, of less than about 40 msecs for a particular patient, correspond to shorter P1 and/or P2 durations (e.g., Block 2 of FIG. 3) which enable optimum defibrillation for a particular patient. Slightly slower time periods of between about 40 msec and 70 msec for item G of the cardiac waveform have been found to correspond to mid-range values for P1 and P2 (e.g., Block 1 of FIG. 3). In another example, F values of less than 3 msec/millivolt (see Table I above) of the cardiac waveform measured correspond to shorter P1 and/or P2 durations (e.g., Block 2 of FIG. 3) which enable optimum defibrillation for a particular patient. Greater values of F (greater than 3 msec/millivolt) correspond with longer P1 and/or P2 durations (e.g., Block 1 or 3 of FIG. 3). Accordingly, FIG. 4 is a chart summarizing collected data for a plurality of patients. In the figure, the column headings comprise:

| Heading | Details |
|---|---|
| No. | Identifies a particular patient |
| G | time period (msec) between points B and C on the cardiac waveform analyzed |
| Block + | Minimum energy/voltage at which a DSW is successful at defibrillating VF, corresponding to the noted Block (i.e., 1, 2 or 3) for table illustrated on FIG. 3. |
| Block − | Maximum energy/voltage at which a DSW fails, corresponding to the noted Block (i.e., 1, 2 or 3) for table illustrated on FIG. 3. |
| PW | Pulse width for P1/P1 in msec, corresponding to the noted Block (i.e., 1, 2 or 3) for table illustrated on FIG. 3, or for 65% tilt. |
| Imp | Impedance of the DSW, corresponding to the noted Block (i.e., 1, 2 or 3) for table illustrated on FIG. 3, or for 65% tilt. |
| 65+ | Minimum energy/voltage at which a DSW is successful at defibrillating VF using fixed tilt of 65% |
| 65− | Maximum energy/voltage at which a DSW fails at defibrillating VF using fixed tilt of 65% |
| Pred Best G | Predicted Block for values for optimal DSW. The measurement and observation conducted related to a G value of less than 40 msec predicting that values in Block 2 were optimal or equal than values of other Blocks or 65% tilt, and 40 msec or greater predicting that other than Block 2 values were optimal or equal to Block 2 values (see FIG. 3 for Block values). |
| Pred Best F | Predicted Block for values for optimal DSB. The measurement and observation conducted related to an F value of less than 3 msec/millivolt predicting that values in Block 2 were optimal or equal than values of other Blocks or 65% tilt, and 3 msec/millivolt or greater predicting that other than Block 2 values were optimal or equal to Block 2 values (see FIG. 3 for Block values). |
| Best | Block (FIG. 3) or tilt associated with values of actual optimal DSW for a particular patient. |
| Results | Did predicted Block or tilt selection for optimal DSW meet actual Block or tilt for optimal DSW? Separate columns for G and F. |

As can be readily apparent by a review of the patient data in FIG. 4, the predicted Block or tilt for selection of values for an optimal DSW, according to some of the embodiments of the present invention, for example using G values, was the actual Block or tilt for selection of values for the actual optimal DSW in 43 out of 48 cases. For example using F values, the predicted Block or tilt for selection of values for an optimal DSW, according to some of the embodiments of the present invention, was the actual Block or tilt for selection of values for the actual optimal DSW in 44 out of 47 cases.

Accordingly, pulse width or tilt selections for such optimal waveforms, e.g., for either or both of the biphasic wave phases, as well as voltage, amperage and energy may be automatically or manually determined and set according to some embodiments of the present invention. For example, cardiac waveform characteristics may be measured and may also be stored by an ICD, by an ICD programmer or other similar device, or by hand and then compared to stored or listed values for such characteristics (e.g., lookup table). The stored/listed values for such characteristics may also include one or more corresponding optimal DSW/defibrillator parameters/variables (e.g., pulse values, peak voltage, peak amperage, energy, tilt). Thus, upon matching, or substantially matching, a measured cardiac waveform characteristic to a stored value for that characteristic, a value for one or more parameters for the optimal DSW/defibrillator may be obtained and then applied to the ICD for application a next time a DSW is necessary for the heart of the particular patient to eliminate VF. As stated earlier, the optimal DSW or parameters thereof, may also depend on the determination of other variables, such as the impedance of the defibrillator/ICD.

A defibrillator/ICD may then be programmed for an optimal DSW and/or optimum parameters either manually (e.g., surgical technician, and the like), for example, with reference to a generated chart or a reference chart, programmed automatically, or programmed via prompts to an operator. Means to accomplish automatic programming (or any of the foregoing) may include software and/or hardware included with the ICD, and/or another device, internal or external to the patient. To that end, the software and/or hardware may be established to conduct cardiac waveform measurements at predetermined, programmed intervals and either automatically program new DSW/defibrillator parameters, or provide an alert to a surgeon/specialist upon patient follow up, for example during direct interrogation or during remote follow up, or provide an alert to the patient. If an alert type system is used, the DSW/defibrillator parameters may be changed by programming during direct interrogation or via communications (e.g., trans-telephonically or other form of remote follow up).

Other aspects of the device, such as the leads and ICD generator (including but not limited to the casing, battery, pulse generator, capacitors, circuitry to provide pacing and a biphasic defibrillator waveform with programmable parameters, e.g., P1 duration and P2 duration, and fixed tilt, and ability to record a waveform) are analogous to commercially available ICD devices, as stated above, such as the St. Jude model V-243.

Accordingly, in one embodiment of the present invention, a method for determining an optimal defibrillation shock waveform for application to the heart of a patient may include: determining a value of at least one characteristic of a cardiac waveform of a patient and selecting, with optional reference to the impedance of the system, a predetermined value for at least one parameter of an optimal defibrillation shock waveform corresponding to the determined value of the at least one characteristic of the cardiac waveform.

Hence, in certain embodiments, the determining of the optimal defibrillation shock waveform includes determining an impedance of an implanted defibrillator system, such as the one described below, for applying the defibrillation shock waveform to the heart of the patient. Further, in certain embodiments, the at least one parameter of an optimal defibrillation shock waveform includes one or more of a total energy of an optimal defibrillation shock waveform, a voltage of an optimal defibrillation shock waveform, a current of an optimal defibrillation shock waveform, a time period for a first phase of an optimal defibrillation shock waveform, a time period for second phase of an optimal defibrillation shock waveform for the patient (e.g., where the first phase is a positive polarity of the defibrillation shock waveform and the second phase is a negative polarity of the defibrillation shock waveform), a time period for a third phase of a defibrillator shock waveform, a tilt of an optimal defibrillation shock waveform, and a polarity of a phase of the defibrillator shock waveform.

In certain embodiments, the cardiac waveform may be an intracardiac electrogram or a surface electrocardiogram. Further, in certain embodiments, the at least one characteristic of the cardiac waveform may be one or more of: a time period between points or portions of the cardiac waveform, such as the waveform provided in FIG. 1, for instance, a slope of a portion of the cardiac waveform, an area under the curve (AUC) of at least a portion of the cardiac waveform, the time period between a pacing stimulus and a point of the cardiac waveform, and a mathematical analysis of the waveform, such as a Fourier transformation, a Bartlett transformation, a wavelet analysis, a relationship between characteristics, and a combination of any of the foregoing.

For example, where the at least one characteristic includes a time period between points or portions of the cardiac waveform, the points may include a peak, a trough, a return to baseline or zero crossing, an inflection point, the initial start of the deflection, and the end of the waveform. In certain embodiments, the time period may include the period between particular points on the cardiac waveform and a height of the cardiac waveform. For instance, the time period between particular points of the cardiac waveform may include the time period between any peak of the cardiac waveform and any trough of the cardiac waveform. Specifically, in certain embodiments, the time period between particular points of the cardiac waveform may include the time period between a first or second peak and/or a first or second trough, for instance, a trough of the cardiac waveform and a subsequent peak of the cardiac waveform. Accordingly, the time period may include the time period between an initial peak of the cardiac waveform and a point at which the cardiac waveform reaches baseline after a first or second trough of the cardiac waveform. Additionally, the time period may include the time period between a first or second peak or first or second trough subsequent to the application of an electrical stimulus.

Specifically, the time period may include a period between particular points of the cardiac waveform such as the time period between the electrical stimulus and a first trough or peak or second trough or second peak of the cardiac waveform. For instance, the time period between particular points of the cardiac waveform may include the time period between the electrical stimulus and a point at which the cardiac waveform reaches baseline after a second trough of the cardiac waveform. In certain embodiments, the time period between particular points of the cardiac waveform may include the time period between a peak of the cardiac waveform and a second trough of the cardiac waveform.

Additionally, the time period may include the time period between an electrical stimulus and a point substantially corresponding to an initial start of deflection of the cardiac waveform. The time period may also include the time period between a point of initial deflection of the cardiac waveform to a subsequent trough or to a subsequent peak of the cardiac waveform. For instance, the time period may include the time period between a point of initial deflection of the cardiac waveform to a first or second trough of the cardiac waveform. Further, the time period may include the time period between a point of initial deflection of the cardiac waveform to a point at which the cardiac waveform substantially reaches baseline, or a point at which the cardiac waveform substantially reaches baseline after a second trough of the cardiac waveform. Accordingly, the time period between particular points of the cardiac waveform may include the time period between an inflection point and another point of the cardiac waveform, wherein the other point is a member may be a peak, a trough, a return to baseline or zero crossing, an inflection point, the initial start of the deflection, and the end of the waveform.

In another embodiment of the present invention, a method for determining an optimal defibrillation shock waveform for application to the heart of a patient to stop ventricular fibrillation or ventricular tachycardia is provided, which may include measuring and/or collecting information for a cardiac waveform of a patient, produced as a result of either an electrical stimulus applied to a heart of the patient (pacing shock/stimulus or DSW) or as the result of intrinsic cardiac activation, determining a characteristic of the waveform, comparing the determined characteristic of the cardiac waveform to a plurality of values for the characteristic, with optional reference to the impedance of the system, wherein each value of the characteristic is associated with a predetermined value for a parameter of an optimal defibrillation shock waveform, and selecting the predetermined value for the parameter of the optimal defibrillation shock waveform based on the comparison.

Figure 5:
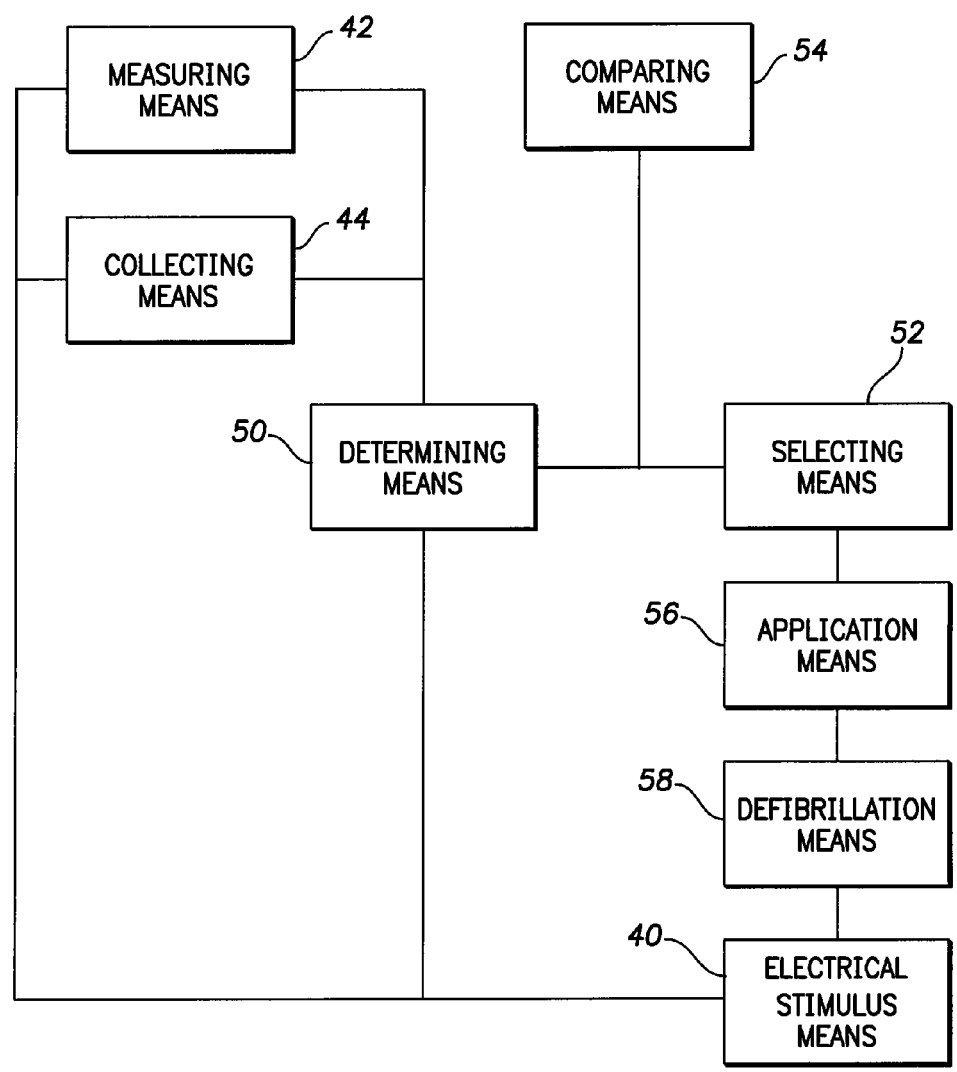

In yet another embodiment of the present invention, as set forth in FIG. 5, a system for determining an optimal defibrillation shock waveform for application to the heart of a patient is provided. The system may include determining means (50) for determining a value of at least one characteristic of a cardiac waveform of a patient and selecting means (52) for selecting a predetermined value for at least one parameter of an optimal defibrillation shock waveform corresponding to the determined value of the at least one characteristic of the cardiac waveform, with optional reference to the impedance of the system. In certain embodiments, the determining means (50) determines one or more of the predetermined values of the at least one parameter for an optimal defibrillation shock waveform, for instance, substantially in real-time and/or after measuring and/or collecting information of the cardiac waveform.

In certain embodiments of the system, the selecting means may be associated with and/or include a comparing means (54) for comparing the determined value of the at least one characteristic of the cardiac waveform and optionally a defibrillator system impedance to a plurality of first values of the at least one characteristic of the cardiac waveform, wherein each first value may be associated with a specific predetermined value for the at least one parameter of an optimal defibrillation shock waveform.

Accordingly, in certain embodiments, a system for determining an optimal defibrillation shock waveform for application to the heart of a patient is provided. The system may include a measuring and/or collecting means for measuring and/or collecting, respectively, information for a cardiac waveform of a patient, produced as a result of either an electrical stimulus applied to a heart of the patient, which may be a pacing shock and/or a defibrillation shock waveform, or as the result of intrinsic cardiac activation. The system may also include: a determining means for determining a characteristic of the waveform; a comparing means for comparing the determined characteristic of the cardiac waveform to a plurality of first values for the characteristic, wherein each first value of the characteristic is associated with a predetermined value for a parameter of an optimal defibrillation shock waveform; and a selecting means for selecting the predetermined value for the parameter of the optimal defibrillation shock waveform based on the comparison.

In certain embodiments, the system may include an application means (56) for applying the selected predetermined value for the at least one parameter to a defibrillation device (58). Additionally, the system may include a measuring and/or collecting means (42 and 44, respectively) for measuring and/or collecting information of the cardiac waveform. The system may also include an electrical stimulus means (40) for applying an electrical stimulus to the heart of a patient, for instance, a means for providing a pacing stimulus or a defibrillation shock waveform to the heart.

In yet another embodiment of the present invention, a system for determining an optimal defibrillation shock waveform for application to the heart of a patient may include measuring and/or collecting means for measuring and/or collecting, respectively, information for a cardiac waveform of a patient, produced as a result of either an electrical stimulus applied to a heart of the patient, which may be a pacing shock/stimulus and/or a DSW, or as the result of intrinsic cardiac activation, determining means for determining a characteristic of the waveform, and comparing means for comparing the determined characteristic of the cardiac waveform and optional system impedance to a plurality of first values for the characteristic. Each first value of the characteristic is associated with a predetermined value for a parameter of an optimal defibrillation shock waveform. The system may also include selecting means for selecting the predetermined value for the parameter of the optimal defibrillation shock waveform based on the comparison.

In yet another embodiment of the present invention, an implantable cardiac defibrillation device is provided which may include electrical shock means for generating and/or applying a defibrillation shock waveform to the heart of a patient, measuring and/or collecting means for measuring and/or collecting, respectively, information for a cardiac waveform of a patient, produced as a result of either an electrical stimulus applied to a heart of the patient, which may be a pacing shock/stimulus and/or a DSW, or as the result of intrinsic cardiac activation, determining means for determining a characteristic of the waveform, and comparing means for comparing the determined characteristic of the cardiac waveform and optional system impedance to a plurality of first values for the characteristic, where each first value of the characteristic is associated with a predetermined value for a parameter of an optimal defibrillation shock waveform.

The system may also include selecting means for selecting the predetermined value for the parameter of the optimal defibrillation shock waveform based on the comparison and configuring means for configuring the electrical shock means to apply the optimal defibrillation shock waveform based on the selected defibrillation parameter.

In yet another embodiment of the present invention, a method for determining an optimal defibrillation shock waveform for a defibrillation device may include measuring and/or collecting information of a cardiac waveform of a patient produced as a result of either an electrical stimulus applied to a heart of the patient, which may be a pacing shock/stimulus and/or a DSW, or as the result of intrinsic cardiac activation, determining at least one characteristic of the waveform, and using the characteristic or combination of characteristics to calculate at least one value for a parameter of an optimal defibrillation shock waveform for the patient. The value for the parameter may also depend upon system impedance.

Having now described a few embodiments of the invention, it should be apparent to those skilled in the art that the foregoing is merely illustrative and not limiting, and it should be understood that numerous changes in analysis, components and configuration of the disclosed embodiments may be introduced without departing from the true spirit of the invention as defined in the appended exemplary claims.

I claim:

1. A method for determining an optimal defibrillation shock waveform for application to the heart of a patient by an implanted defibrillation system, said method comprising:

obtaining a cardiac electrogram of the patient corresponding to at least one complete heart cycle, wherein the cardiac electrogram is a measure of the varying electrical potential between two electrodes positioned adjacent the heart and is characterized by a baseline, at least one peak above the baseline, and at least one trough below the baseline;

determining a value of at least one characteristic of the cardiac electrogram; and selecting a predetermined value for at least one parameter of an optimal defibrillation shock waveform for subsequent delivery by the implanted defibrillation system, wherein the at least one parameter is based on the determined value of the at least one characteristic of the cardiac electrogram;

wherein the at least one parameter defines the optimal defibrillation shock waveform and is selected from a group consisting of: a total energy of an optimal defibrillation shock waveform, a voltage of an optimal defibrillation shock waveform, a current of an optimal defibrillation shock waveform, a time period for a first phase of an optimal defibrillation shock waveform, a time period for second phase of an optimal defibrillation shock waveform for the patient, a time period for a third phase of a defibrillator shock waveform, a tilt of an optimal defibrillation shock waveform, and a polarity of a phase of a defibrillator shock waveform.

2. The method according to claim 1, wherein selecting the predetermined value for the at least one parameter of the optimal defibrillation shock waveform includes making reference to a measured defibrillator system impedance.

3. The method according to claim 1, wherein selecting the predetermined value for the at least one parameter of the optimal defibrillation shock waveform comprises comparing the determined value of the at least one characteristic of the cardiac electrogram to a plurality of values of the at least one characteristic of the cardiac electrogram, wherein each value is associated with a specific predetermined value for the at least one parameter of an optimal defibrillation shock waveform.

4. The method according to claim 1, further comprising applying the selected predetermined value for the at least one parameter to the defibrillation system.

5. The method according to claim 1, wherein prior to determining the value of the at least one characteristic of the cardiac electrogram, the method further comprises measuring and/or collecting information of the cardiac electrogram.

6. The method according to claim 1, wherein the cardiac electrogram is produced either as the result of an electrical stimulus applied to the heart of the patient, which may be from a pacing shock/stimulus and/or a defibrillation shock waveform, or as the result of intrinsic cardiac activation.

7. The method according to claim 1, further comprising determining one or more of the predetermined values of the at least one parameter for an optimal defibrillation shock waveform.

8. The method according to claim 7, wherein the one or more predetermined values of the at least one parameter of an optimal defibrillation shock waveform is determined substantially in real-time.

9. The method according to claim 7, wherein the one or more predetermined values of the at least one parameter of an optimal defibrillation shock waveform is determined after measuring and/or collecting information of the cardiac electrogram.

10. The method according to claim 1, wherein the cardiac electrogram is an intracardiac electrogram.

11. The method according to claim 1, wherein the cardiac electrogram is a surface electrocardiogram.

12. The method according to claim 1, wherein the at least one characteristic of the cardiac waveform is selected from a group consisting of: a time period between points or portions of the cardiac electrogram, a slope of a portion of the cardiac electrogram, an area under the curve (AUC) of at least a portion of the cardiac electrogram, a time period between a pacing stimulus and a point of the cardiac electrogram, and a mathematical analysis of the electrogram.

13. The method according to claim 12, where points include a peak above baseline, a trough below baseline, a return to baseline or zero crossing, an inflection point, the initial start of the deflection, and the end of the electrogram.

14. The method according to claim 12, wherein the mathematical analysis is selected from the group consisting of: a Fourier transformation, a Bartlett transformation, a relationship between characteristics, and a wavelet analysis, or a combination thereof.

15. The method according to claim 14, wherein the relationship comprises a time period between particular points on the cardiac electrogram and a height of the cardiac electrogram.

16. The method according to claim 12, wherein the time period between points of the cardiac electrogram comprises the time period between a trough of the cardiac electrogram and a subsequent peak of the cardiac electrogram.

17. The method according to claim 16, wherein the trough comprises a first trough of the cardiac electrogram after application of the electrical stimulus.

18. The method according to claim 12, wherein the time period between particular points of the cardiac electrogram comprises the time period between the electrical stimulus and a point substantially corresponding to an initial start of deflection of the cardiac electrogram.

19. The method according to claim 12, wherein the time period between particular points of the cardiac electrogram comprises the time period between the electrical stimulus and a first trough of the cardiac electrogram.

20. The method according to claim 12, wherein the time period between particular points of the cardiac electrogram comprises the time period between the electrical stimulus and a first peak of the cardiac electrogram.

21. The method according to claim 12, wherein the time period between particular points of the cardiac electrogram comprises the time period between the electrical stimulus and a second trough of the cardiac electrogram.

22. The method according to claim 12, wherein the time period between particular points of the cardiac electrogram comprises the time period between the electrical stimulus and a point at which the cardiac electrogram reaches baseline after a second trough of the cardiac electrogram.

23. The method according to claim 12, wherein the time period between particular points of the cardiac electrogram comprises the time period between a peak of the cardiac electrogram and a second trough of the cardiac electrogram.

24. The method according to claim 12, wherein the time period between particular points of the cardiac electrogram comprises the time period between any peak of the cardiac electrogram and any trough of the cardiac electrogram.

25. The method according to claim 12, wherein the time period between particular points of the cardiac electrogram comprises the time period between an initial peak of the cardiac electrogram and a point at which the cardiac electrogram reaches baseline after a second trough of the cardiac electrogram.

26. The method according to claim 12, wherein the time period between particular points of the cardiac electrogram comprises the time period between a point of initial deflection of the cardiac electrogram to a first trough of the cardiac electrogram.

27. The method according to claim 12, wherein the time period between particular points of the cardiac electrogram comprises the time period between a point of initial deflection of the cardiac electrogram to a subsequent peak of the cardiac electrogram.

28. The method according to claim 12, wherein the time period between particular points of the cardiac electrogram comprises the time period between a point of initial deflection of the cardiac electrogram to a subsequent trough of the cardiac electrogram.

29. The method according to claim 12, wherein the time period between particular points of the cardiac electrogram comprises the time period between a point of initial deflection of the cardiac electrogram to a second trough of the cardiac electrogram.

30. The method according to claim 12, wherein the time period between particular points of the cardiac electrogram comprises the time period between a point of initial deflection of the cardiac electrogram to a point at which the cardiac electrogram substantially reaches baseline.

31. The method according to claim 30, wherein the point at which the cardiac electrogram substantially reaches baseline occurs after a second trough of the cardiac electrogram.

32. The method according to claim 12, wherein the time period between particular points of the cardiac electrogram compromises the time period between an inflection point and another point of the cardiac electrogram, wherein the other point is a member selected from a group consisting of a peak, a trough, a return to baseline or zero crossing, an inflection point, the initial start of the deflection, and the end of the electrogram.

33. The method according to claim 1, wherein determining the optimal defibrillation shock waveform includes determining an impedance of an implanted defibrillator system for applying the defibrillation shock waveform to the heart of the patient.

34. The method according to claim 1, wherein the first phase comprises a positive polarity of the defibrillation shock waveform and the second phase comprises a negative polarity of the defibrillation shock waveform.

35. A method for determining an optimal defibrillation shock waveform for application to the heart of a patient by an implanted defibrillation system comprising:
measuring and/or collecting information for a cardiac waveform of a patient, produced as a result of either an electrical stimulus applied to a heart of the patient or as the result of intrinsic cardiac activation, wherein the cardiac waveform is a cardiac electrogram of the patient corresponding to at least one complete heart cycle, wherein the cardiac electrogram is a measure of the varying electrical potential between two electrodes positioned adjacent the heart and is characterized by a baseline, at least one peak above the baseline, and at least one trough below the baseline;
determining at least one characteristic of the electrogram;
comparing the determined characteristic(s) of the cardiac electrogram to a plurality of values for the characteristic, wherein each value of the characteristic is associated with a predetermined value for a parameter of an optimal defibrillation shock waveform with optional reference to the defibrillator system impedance; and
selecting the predetermined value for the parameter of the optimal defibrillation shock waveform for subsequent delivery by the implanted defibrillation system, wherein the parameter is selected based on the comparison;
wherein the at least one parameter defines the optimal defibrillation shock waveform and is selected from a group consisting of: a total energy of an optimal defibrillation shock waveform, a voltage of an optimal defibrillation shock waveform, a current of an optimal defibrillation shock waveform, a time period for a first phase of an optimal defibrillation shock waveform, a time period for second phase of an optimal defibrillation shock waveform for the patient, a time period for a third phase of a defibrillator shock waveform, a tilt of an optimal defibrillation shock waveform, and a polarity of a phase of a defibrillator shock waveform.

36. A system for determining an optimal defibrillation shock waveform for application to the heart of a patient by an implanted defibrillation system, said system comprising:
means for obtaining a cardiac electrogram of the patient corresponding to at least one complete heart cycle, wherein the cardiac electrogram is a measure of the varying electrical potential between two electrodes positioned adjacent the heart and is characterized by a baseline, at least one peak above the baseline, and at least one trough below the baseline;
determining means for determining a value of at least one characteristic of the cardiac electrogram; and
selecting means for selecting a predetermined value for at least one parameter of an optimal defibrillation shock waveform for subsequent delivery by the implanted defibrillation system, wherein the at least one parameter is based on the determined value of the at least one characteristic of the cardiac electrogram with optional reference to the defibrillator system impedance;
wherein the at least one parameter defines the optimal defibrillation shock waveform and is selected from a group consisting of: a total energy of an optimal defibrillation shock waveform, a voltage of an optimal defibrillation shock waveform, a current of an optimal defibrillation shock waveform, a time period for a first phase of an optimal defibrillation shock waveform, a time period for second phase of an optimal defibrillation shock waveform for the patient, a time period for a third phase of a defibrillator shock waveform, a tilt of an optimal defibrillation shock waveform, and a polarity of a phase of a defibrillator shock waveform.

37. The system according to claim 36, wherein the selecting means comprises comparing means for comparing the determined value of the at least one characteristic of the cardiac electrogram and optionally a defibrillator system impedance to a plurality of first values of the at least one characteristic of the cardiac electrogram, wherein each first value is associated with a specific predetermined value for the at least one parameter of an optimal defibrillation shock waveform.

38. The system according to claim 36, further comprising application means for applying the selected predetermined value for the at least one parameter to the defibrillation system.

39. The system according to claim 36, further comprising measuring and/or collecting means for measuring and/or collecting information of the cardiac electrogram.

40. The system according to claim 36, further comprising electrical stimulus means for applying an electrical stimulus to the heart of the patient.

41. The system according to claim 36, wherein a determining means determines one or more of the predetermined values of the at least one parameter for an optimal defibrillation shock waveform.

42. The system according to claim 41, wherein the one or more predetermined values of the at least one parameter of an optimal defibrillation shock waveform is determined substantially in real-time.

43. The system according to claim 41, wherein the one or more predetermined values of the at least one parameter of an optimal defibrillation shock waveform is determined after measuring and/or collecting information of the cardiac electrogram.

44. The system according to claim 40, wherein the electrical stimulus comprises a pacing stimulus or a defibrillation shock waveform.

45. The system according to claim 36, wherein the cardiac electrogram is an intracardiac electrogram.

46. The system according to claim 36, wherein the cardiac electrogram is a surface electrocardiogram.

47. The system according to claim 36, wherein the at least one characteristic of the cardiac electrogram is selected from a group consisting of: a time period between points or portions of the cardiac electrogram, a slope of a portion of the cardiac electrogram, an area under the curve (AUC) of at least a portion of the cardiac electrogram, a time period between a pacing stimulus and a point of the cardiac electrogram, and a mathematical analysis of the electrogram.

48. The system according to claim 47, where points can include a peak above baseline, a trough below baseline, a return to baseline or zero crossing, an inflection point, the initial start of the deflection, and the end of the electrogram.

49. The system according to claim 47, wherein the mathematical analysis is selected from the group consisting of: a Fourier transformation, a Bartlett transformation, a wavelet analysis, a relationship between characteristics, and a combination of any of the foregoing.

50. The system according to claim 49, wherein the relationship comprises a time period between particular points on the cardiac electrogram and a height of the cardiac electrogram.

51. The system according to claim 47, wherein the time period between points of the cardiac electrogram comprises the time period between a trough of the cardiac electrogram and a subsequent peak of the cardiac electrogram.

52. The system according to claim 51, wherein the trough comprises a first trough of the cardiac electrogram after application of the electrical stimulus.

53. The system according to claim 47, wherein the time period between particular points of the cardiac electrogram comprises the time period between the electrical stimulus and a point substantially corresponding to an initial start of deflection of the cardiac electrogram.

54. The system according to claim 47, wherein the time period between particular points of the cardiac electrogram comprises the time period between the electrical stimulus and a first trough of the cardiac electrogram.

55. The system according to claim 47, wherein the time period between particular points of the cardiac electrogram comprises the time period between the electrical stimulus and a first peak of the cardiac electrogram.

56. The system according to claim 47, wherein the time period between particular points of the cardiac electrogram comprises the time period between the electrical stimulus and a second trough of the cardiac electrogram.

57. The system according to claim 47, wherein the time period between particular points of the cardiac electrogram comprises the time period between the electrical stimulus and a point at which the cardiac electrogram reaches baseline after a second trough of the cardiac electrogram.

58. The system according to claim 47, wherein the time period between particular points of the cardiac electrogram comprises the time period between a peak of the cardiac electrogram and a second trough of the cardiac electrogram.

59. The system according to claim 47, wherein the time period between particular points of the cardiac electrogram comprises the time period between any peak of the cardiac electrogram and any trough of the cardiac electrogram.

60. The system according to claim 47, wherein the time period between particular points of the cardiac electrogram comprises the time period between an initial peak of the cardiac electrogram and a point at which the cardiac electrogram reaches baseline after a second trough of the cardiac electrogram.

61. The system according to claim 47, wherein the time period between particular points of the cardiac electrogram comprises the time period between a point of initial deflection of the cardiac electrogram to first trough of the cardiac electrogram.

62. The system according to claim 47, wherein the time period between particular points of the cardiac electrogram comprises the time period between a point of initial deflection of the cardiac electrogram to a subsequent peak of the cardiac electrogram.

63. The system according to claim 47, wherein the time period between particular points of the cardiac electrogram comprises the time period between a point of initial deflection of the cardiac electrogram to a subsequent trough of the cardiac electrogram.

64. The system according to claim 47, wherein the time period between particular points of the cardiac electrogram comprises the time period between a point of initial deflection of the cardiac electrogram to second trough of the cardiac electrogram.

65. The system according to claim 47, wherein the time period between particular points of the cardiac electrogram comprises the time period between a point of initial deflection of the cardiac electrogram to a point at which the cardiac electrogram substantially reaches baseline.

66. The system according to claim 65, wherein the point at which the cardiac electrogram substantially reaches baseline occurs after a second trough of the cardiac electrogram.

67. The system according to claim 45, wherein the time period between particular points of the cardiac electrogram compromises the time period between an inflection point and another point of the cardiac electrogram, wherein the other point is a member selected from a group consisting of a peak, a trough, a return to baseline or zero crossing, an inflection point, the initial start of the deflection, and the end of the electrogram.

68. The system according to claim 36, wherein determining the optimal defibrillation shock waveform includes determining an impedance of an implanted defibrillator system for applying the defibrillation shock waveform to the heart of the patient.

69. The system according to claim 36, wherein the first phase comprises a positive polarity of the defibrillation shock waveform and the second phase comprises a negative polarity of the defibrillation shock waveform.

70. A system for determining an optimal defibrillation shock waveform for application to the heart of a patient by an implanted defibrillation system, said system comprising:
 measuring and/or collecting means for measuring and/or collecting, respectively, information for a cardiac waveform of a patient, produced as a result of either an electrical stimulus applied to a heart of the patient, which may be a pacing shock and/or a defibrillation shock waveform, or as the result of intrinsic cardiac activation, wherein the cardiac waveform is a cardiac electrogram of the patient corresponding to at least one complete heart cycle, wherein the cardiac electrogram is a measure of the varying electrical potential between two electrodes positioned adjacent the heart and is characterized by a baseline, at least one peak above the baseline, and at least one trough below the baseline;
 determining means for determining a characteristic of the electrogram;
 comparing means for comparing the determined characteristic of the cardiac electrogram to a plurality of first values for the characteristic, wherein each first value of the characteristic is associated with a predetermined value for a parameter of an optimal defibrillation shock waveform; and
 selecting means for selecting the predetermined value for the parameter of the optimal defibrillation shock waveform for subsequent delivery by the implanted defibrillation system, wherein the parameter is selected based on the comparison;
 wherein the at least one parameter defines the optimal defibrillation shock waveform and is selected from a group consisting of: a total energy of an optimal defibrillation shock waveform, a voltage of an optimal defibrillation shock waveform, a current of an optimal defibrillation shock waveform, a time period for a first phase of an optimal defibrillation shock waveform, a time period for second phase of an optimal defibrillation shock waveform for the patient, a time period for a third phase of a defibrillator shock waveform, a tilt of an optimal defibrillation shock waveform, and a polarity of a phase of a defibrillator shock waveform.

71. A method for determining an optimal defibrillation shock waveform for an implanted defibrillation device, the method comprising:
 measuring and/or collecting information of a cardiac waveform of a patient produced as a result of either an electrical stimulus applied to a heart of the patient or as the result of intrinsic cardiac activation, wherein the cardiac waveform is a cardiac electrogram of the patient corresponding to at least one complete heart cycle, wherein the cardiac electrogram is a measure of the varying electrical potential between two electrodes positioned adjacent the heart and is characterized by a baseline, at least one peak above the baseline, and at least one trough below the baseline;
 determining at least one characteristic of the electrogram; and
 using the characteristic or combination of characteristics to calculate at least one value for a parameter of an optimal defibrillation shock waveform for subsequent delivery by the implanted defibrillation device, wherein the at least one parameter is far the patient with optional reference to the defibrillator system impedance;
 wherein the at least one parameter defines the optimal defibrillation shock waveform and is selected from a group consisting of: a total energy of an optimal defibrillation shock waveform, a voltage of an optimal defibrillation shock waveform, a current of an optimal defibrillation shock waveform, a time period for a first phase of an optimal defibrillation shock waveform, a time period for second phase of an optimal defibrillation shock waveform for the patient, a time period for a third phase of a defibrillator shock waveform, a tilt of an optimal defibrillation shock waveform, and a polarity of a phase of a defibrillator shock waveform.

* * * * *